(12) United States Patent
Doerr (10) Patent No.: US 8,565,895 B2
(45) Date of Patent: Oct. 22, 2013

(54) IMPLANTABLE ELECTRODE LEAD AND HYDROGEL SENSOR

(75) Inventor: Thomas Doerr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 172 days.

(21) Appl. No.: 13/191,347

(22) Filed: Jul. 26, 2011

(65) Prior Publication Data

US 2012/0078330 A1 Mar. 29, 2012

Related U.S. Application Data (60) Provisional application No. 61/385,565, filed on Sep. 23, 2010.

(51) Int. Cl.
*A61N 1/02* (2006.01)

(52) U.S. Cl.
USPC .......................................... 607/116

(58) Field of Classification Search
USPC ............... 607/116, 119, 126–128; 600/347
See application file for complete search history.

(56) References Cited

U.S. PATENT DOCUMENTS 5,869,078 A * 2/1999 Baudino ....................... 424/423

FOREIGN PATENT DOCUMENTS

| DE | 19800697 | 7/1999 |
|---|---|---|
| DE | 102004061732 A1 | 7/2006 |
| DE | 102005039040 | 2/2007 |
| DE | 202006020517 | 11/2008 |
| EP | 0306442 | 3/1989 |
| EP | 2158840 A2 | 3/2010 |
| WO | 2004062714 A1 | 7/2004 |

OTHER PUBLICATIONS

European Search Report dated Feb. 21, 2012, 8 pages.

* cited by examiner

*Primary Examiner* — Amanda Patton
(74) *Attorney, Agent, or Firm* — ARC IP Law, PC; Joseph J. Mayo (57) ABSTRACT

An implantable electrode lead that includes a distal section having at least one electrode for transmitting electrical energy between the electrode lead and its surroundings. The electrode lead includes at least one hydrogel capsule that is thermally coupled to the electrode, the hydrogel capsule having a water-permeable wall that forms a cavity containing a hydrogel having a temperature-dependent swelling capacity, the wall of the hydrogel capsule being designed such that it can adapt to the volume of the hydrogel. Further relates to an electrode lead assembly, in the case of which a guide element is provided for guiding an electrode lead having a hydrogel capsule of this type. Further relates to a hydrogel sensor that comprises a hydrogel capsule of this type. Furthermore, at least one embodiment of the invention relates to methods used to determine the size of the hydrogel capsule for the purpose of determining the temperature of an electrode, or environment, that is thermally coupled to the hydrogel capsule.

16 Claims, 6 Drawing Sheets

IMPLANTABLE ELECTRODE LEAD AND HYDROGEL SENSOR

This application claims the benefit of U.S. Provisional Patent Application 61/385,565, filed on Sep. 23, 2010, the specification of which is hereby incorporated herein by reference.

BACKGROUND OF THE INVENTION

1. Field of the Invention

One or more embodiments of the invention are based in the field of medical engineering and relates to an implantable electrode lead, and an electrode lead assembly. One or more embodiments of the invention furthermore relates to an implantable hydrogel sensor and its use. Furthermore, at least one embodiment of the invention relates to a method to determine the temperature of the electrode of an electrode lead, and a method for operating a nuclear magnetic resonance tomograph, and its use.

2. Description of the Related Art

Electrode leads of the type in question are known in various embodiments and are used routinely e.g. in the field of electrophysiology to detect and treat conduction defects in the heart or the nervous system. Depending on the application, they are also referred to e.g. as a stimulation electrode, a cardiac pacemaker electrode, an ICD electrode (ICD=implantable cardioverter) or an electrophysiology catheter. They have been described numerous times in patent literature. Reference is made in this context, merely for the purpose of providing examples, to the publications DE 10 2005 039 040 A1, DE 198 00 697 A1, DE 20 2006 020 517 U1, and EP 0 306 442.

As is known per se to a person skilled in the art, electrode leads that are present in a patient's body can cause problems during an examination using a nuclear resonance tomograph. In nuclear resonance tomography or magnetic resonance tomography (MRT=magnetic resonance tomography), atomic nuclei are forced by strong magnetostatic fields to precess about the field direction, and they undergo resonant excitation by high frequency electromagnetic alternating fields. When the alternating fields are shut off, the atomic nuclei return to their original direction; the relaxation times are characteristic for various types of tissue, thereby making exact imaging possible.

However, when a patient has an implanted electrode lead, there is a risk that its electrodes and the surrounding tissue layers will heat up. This is caused by electrical induction currents that are generated by the strong electromagnetic alternating fields of the nuclear resonance tomograph. For this reason, the diagnostic utility of an examination based on nuclear resonance tomography must be weighed carefully against the risk of disadvantageous side effects. This situation is made more difficult by the fact that the heating of the electrodes depends on the particular scan parameters of the examination and, in particular, on the positioning of the electrode lead in the electromagnetic alternating field, thereby often rendering it impossible to make reliable prognoses in clinical practice. As a result, patients who have an implanted electrode lead are typically denied an examination using nuclear resonance tomography, which is harmless per se.

The object of the at least one embodiment of the invention, therefore, is to provide an implantable electrode lead for the medical application, using which an examination based on nuclear resonance tomography can be performed in a safe, reliable manner. In addition, an electrode lead of this type should be easy to use and cost effective to manufacture in high-volume production. These and further objects are solved according to the proposed invention by an electrode lead and an electrode lead assembly having the features as described and claimed herein. Advantageous embodiments of embodiments of the invention are also described and claimed herein.

BRIEF SUMMARY OF THE INVENTION

According to at least one embodiment of the invention, an implantable electrode lead for medical applications is shown. The expression "implantable", as used herein, refers to a permanent or brief, temporary stay in a patient's body e.g. only for the duration of an examination. The electrode lead can be present in a variety of embodiments e.g. it can be a stimulation electrode, in particular for nerve stimulation, a cardiac pacemaker electrode, an ICD electrode, an electrophysiology catheter, or an electrode for measuring brain potentials or the like. The list is not conclusive, as one skilled in the art will appreciate.

Generically, the electrode lead includes a distal section having at least one electrically conductive surface region for receiving electrical signals or for emitting electrical pulses i.e. to transmit electrical energy between the electrode lead and its surroundings. Here and henceforth the electrically conductive surface region will be referred to as the "electrode". Another typical term therefore would be "pole". The at least one electrode of the electrode lead is connected to an electrical lead which can be electrically connected, at a proximal end of the electrode lead, to an electrical device e.g. a cardiac pacemaker. The surface of the electrode lead is typically electrically insulated, with the exception of the at least one electrode.

According to the at least one embodiment of the invention, the electrode lead is characterized mainly in that the electrode lead includes at least one hydrogel capsule that is thermally coupled to the electrode, wherein the hydrogel capsule has a wall that is water-permeable at least in sections, the wall forming a cavity containing a hydrogel having a temperature-dependent swelling capacity. The wall of the hydrogel capsule is designed such that it can adapt to the volume of the hydrogel, the volume being dependent on the water content. This means that the hydrogel capsule increases in size when the volume of the hydrogel increases, and shrinks when the volume of the hydrogel decreases, without appreciably impairing the change in volume of the hydrogel. To this end, the wall of the hydrogel capsule is composed e.g. of an elastically deformable material, the modulus of elasticity of which is of a magnitude that is suitable for this purpose. The hydrogel capsule or the hydrogel contained therein is thermally coupled to the electrode, thereby enabling the temperature of the hydrogel to follow a change in temperature of the electrode. The wall of the hydrogel capsule has sufficient thermal conductivity for this purpose. If the electrode lead has two or more electrodes, each electrode may be thermally coupled to a separate hydrogel capsule.

The expression "at least in sections" means that only a part of the wall or the entire wall of the hydrogel capsule is designed to be water-permeable.

In another embodiment, only the distal base of the hydrogel capsule is water-permeable.

In another embodiment, the electrode lead or the guide wire itself that is inserted therein contains a water reservoir (720) that is connected via a diaphragm (730) or duct to the hydrogel capsule (710) and so the water-permeable wall is formed, while the rest of the hydrogel capsule is water-impermeable. Depending on the heating that occurs, the water content can therefore move between the hydrogel capsule and the water reservoir (740), and the ratio of the water content can be evaluated accordingly using MRT image evaluation. This method offers the advantage that it can also be used in a component, such as the guide wire, that is insulated against the bodily fluid, and that no calibration or only very simple calibration is required to evaluate the ratio of the water content.

In concordance with the typical use of the term hydrogel, in this case it is a substance that can absorb water but itself is insoluble in water. These are typically hydrophilic polymers, the chains of which are connected to a three-dimensional network by covalent bonds, ionic bonds, and/or physical interactions. Due to the hydrophilic components, hydrogels are capable of reversibly binding water molecules. In the present invention, only those hydrogels are used that have a temperature-dependent swelling capacity. This means that the water content and, therefore, the volume of the hydrogel changes as the temperature of the hydrogel changes.

The electrode lead according to at least one embodiment of the invention advantageously makes it possible to easily and safely determine the temperature of the thermally coupled electrode by measuring an outer dimension or the volume of the hydrogel capsule. A particular advantage of the embodiment results from the fact that the hydrogel is easily recognized in a nuclear resonance tomographic image due to the very high water content, thereby making it possible to easily evaluate the outer dimension of the hydrogel capsule in the nuclear resonance tomographic image. The wall thickness of the capsule is typically negligibly small compared to the expansion of the hydrogel. It is therefore possible to continually monitor the temperature of the thermally coupled electrode of the electrode lead during a nuclear resonance tomographic examination in particular. The hydrogel contained in the hydrogel capsule is therefore used as a sensor to detect the temperature of the electrode in the electrode lead.

According to another embodiment of the electrode lead, the hydrogel capsule containing the hydrogel is disposed in the vicinity of the electrode or abuts it, to achieve good thermal coupling between the electrode and the hydrogel. The hydrogel capsule preferably has physical contact with the electrode, to ensure efficient heat transfer via thermal conduction.

The electrode may be implemented as a point or tip electrode disposed on a distal end of the electrode lead since, in this case, it is particularly important to monitor the electrode temperature due to the small electrode surface and the associated high risk of tissue damage occurring.

As mentioned above, the swelling capacity of the hydrogel is dependent on its temperature. According to an another embodiment of the electrode lead, the swelling capacity of the hydrogel diminishes as the temperature of the hydrogel increases, and so the water content and, therefore, the volume of the hydrogel shrinks when the temperature of the electrode increases. Conversely, the swelling capacity of the hydrogel increases as the temperature of the hydrogel decreases, and so the water content and, therefore, the volume of the hydrogel increases when the temperature of the electrode decreases. The hydrogel may be selected such that the swelling capacity of the hydrogel decreases by at least 30% when the temperature of the hydrogel increases by 10° C., thereby making it possible to reliably and safely detect changes in the temperature of the electrode, which occur frequently in practice. In general, the hydrogel can be selected such that the temperature changes of the thermally coupled electrode, which typically occur depending on the particular application, are associated with a large change in volume of the hydrogel or the hydrogel capsule.

The hydrogel may be a polymer that is composed of or based on one or more substances selected from the group comprising acrylamide, metacrylamide, dimethylaminoethyl methacrylate, and a derivative of these substances. Likewise, it can be preferable for the hydrogel to be composed of or based on poly(N-isopropylacrylamide) and/or poly-N-isopropylacrylamide-co-allylamine. Particularly in at least one embodiment, the hydrogel is poly(N-isopropylacrylamide) or PNIPAM with poly-p-dioxanon as the hard segment.

The wall of the hydrogel capsule containing the hydrogel may be composed of a polyester, in particular of one or more substances selected from the group composed of poly-L-lactide (PLLA), poly-DL-lactide (PDLLA), poly(lactide-co-glycolide) (PLGA), poly-3-hydroxybutyrate (P3HB), poly-4-hydroxybutyrate (P4HB), and derivatives and copolymers thereof. The wall of the hydrogel capsule may be composed of Parylene, in particular Parylene C or other derivatives, particularly Parylene having small pinholes.

According to another embodiment of the electrode lead, the hydrogel capsule is fully accommodated in the electrode lead, wherein the wall of the hydrogel capsule forms a surface region of the electrode lead, and therefore the handling of the electrode lead is not impaired by the hydrogel capsule.

According to another embodiment of the electrode lead, the hydrogel capsule, and the hydrogel contained therein, is provided with a passage for accommodating a guide means for the electrode lead, and therefore the handling of the electrode lead is not impaired by the hydrogel capsule, and the electrode lead can be installed in the conventional manner.

At least one embodiment of the invention furthermore relates to an electrode lead assembly for a medical application, which includes an implantable electrode lead having a distal section with at least one electrode for transmitting electrical energy between the electrode lead and its surroundings, and a guide means, which can be inserted into the electrode lead, for guiding the electrode lead.

The electrode lead is characterized mainly by the fact that the guide means includes at least one hydrogel capsule which is disposed such that it is thermally coupled to the electrode in a position that is suitable for guiding the electrode lead. The hydrogel capsule is provided with a water-permeable wall that forms a cavity in which a hydrogel having a temperature-dependent swelling capacity is contained, the wall being designed such that it can adapt to the volume of the hydrogel. Reference is made to the descriptions presented above with regard for the hydrogel and the hydrogel capsule, to avoid unnecessary repetition.

According to another embodiment, the hydrogel capsule is connected to a water reservoir via a water-permeable wall such as a diaphragm, or a duct or an opening. The walls that are not adjacent to the water reservoir can be water-permeable or water-impermeable. Due to the water reservoir, the measurement method using the hydrogel capsule becomes independent of contact with bodily fluid.

At least one embodiment of the invention furthermore relates to an implantable hydrogel sensor which includes a hydrogel capsule having a water-permeable wall that forms a cavity containing a hydrogel having a temperature-dependent swelling capacity. The wall is designed such that it can adapt to the volume of the hydrogel. Reference is made to the descriptions presented above with regard for the hydrogel and its wall, to avoid unnecessary repetition. An outer dimension of the hydrogel sensor therefore changes due to the absorption or release of water depending on the ambient temperature of the hydrogel sensor. The hydrogel that is used can be selected specifically depending on the changes in ambient temperature that typically occur for the particular application, and therefore the temperature changes are associated with a large change in volume of the hydrogel sensor. As described above, the size of the hydrogel capsule can be determined easily by evaluating a nuclear resonance tomographic image.

At least one embodiment of the invention furthermore relates to the use of an implantable hydrogel sensor, according to the invention, for determining the ambient temperature of the implanted hydrogel sensor.

A method for determining the ambient temperature of an implantable hydrogel sensor according to at least one embodiment of the invention follows. According to the method, a hydrogel sensor is provided, an outer dimension of the hydrogel capsule is measured, and the temperature of the surroundings of the hydrogel capsule is ascertained on the basis of the outer dimension of the hydrogel capsule.

At least one embodiment of the invention furthermore relates to a method for determining the temperature of an electrode of an implantable electrode lead. According to the method, an electrode lead is provided, an outer dimension of the at least one hydrogel capsule is measured, and the temperature of the thermally coupled electrode is ascertained on the basis of the outer dimension of the hydrogel capsule. In particular, a change in the temperature of the electrode can be determined on the basis of a change in the outer dimension of the hydrogel capsule. The outer dimension of the hydrogel capsule may be determined via evaluation of a nuclear resonance tomographic image.

At least one embodiment of the invention furthermore relates to a method for positioning an electrode lead, in the case of which an electrode lead assembly is provided, and the guide means are moved into a position that is suitable for guiding the electrode lead, and in which the hydrogel capsule is thermally coupled to the electrode. Next, an outer dimension of the hydrogel capsule is measured while the electrode lead is being guided by the guide means, and the temperature of the thermally coupled electrode is ascertained on the basis of the outer dimension of the hydrogel capsule. The outer dimension of the hydrogel capsule may be determined via evaluation of a nuclear resonance tomographic image. Once the electrode lead has been positioned, the guide means can be removed.

At least one embodiment of the invention furthermore relates to a method for operating a nuclear resonance tomograph, in the case of which an implantable electrode lead according to the invention is provided, an external dimension of the hydrogel capsule is measured, and the temperature of the thermally coupled electrode is ascertained on the basis of the outer dimension of the hydrogel capsule. The outer dimension of the hydrogel capsule may be determined via evaluation of a nuclear resonance tomographic image. On the basis of the temperature of the electrode, one or more of the following steps are carried out next:

Reduce the intensity of electromagnetic alternating fields used for the resonant excitation of atomic nuclei if the temperature of the electrode exceeds a predeterminable first threshold value;

Shut off the electromagnetic alternating fields if the temperature of the electrode exceeds a predeterminable second temperature threshold value which can be identical to the first temperature threshold value;

Display the temperature of the electrode in a graphical display device of the nuclear resonance tomograph;

Apply an electrical pulse to the electrode to ablate surrounding bodily tissue.

At least one embodiment of the invention furthermore relates to the use of a nuclear resonance tomograph to determine an outer dimension of a hydrogel capsule that is thermally coupled to an electrode of an implantable electrode lead according to the invention.

It is understood that the various embodiments and designs of the subjects according to the invention can be realized individually or in any combination. In particular, the features mentioned above and to be described below can be used not only in the combinations described, but also in other combinations or alone, without leaving the scope of embodiments of the invention.

BRIEF DESCRIPTION OF THE DRAWINGS

At least one embodiment of the invention is explained in greater detail with reference to the attached drawings. Elements that are the same or similar-acting are labeled using the same reference numerals. The drawings show.

DETAILED DESCRIPTION OF THE INVENTION

Figure 5:
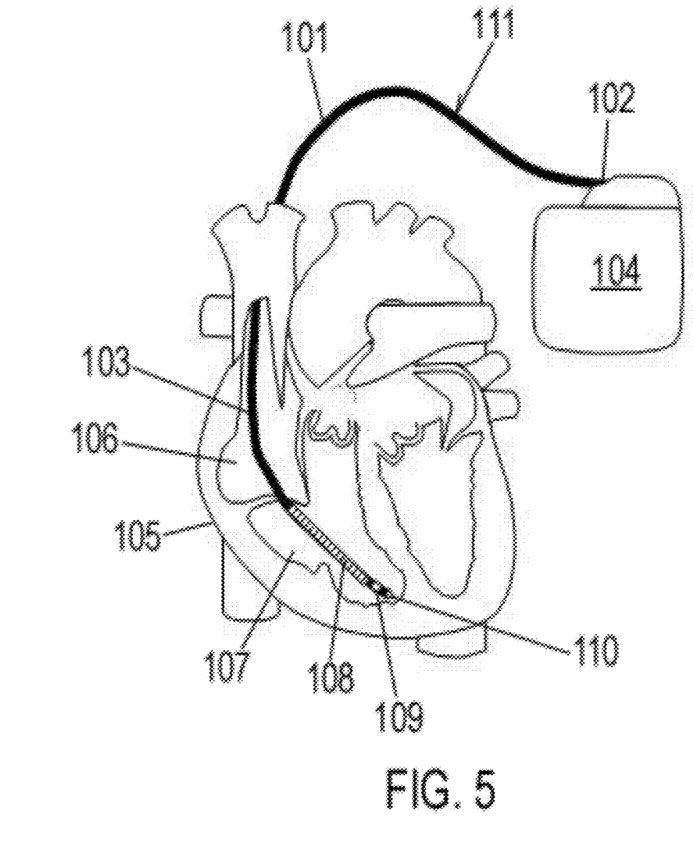
FIG. 5 a schematic depiction to illustrate a conventional, permanently implanted electrode lead.

FIG. 5 shall be considered first; it shows a schematic depiction of an electrode lead 101 that is permanently implanted in a heart 105 and is well-known in the prior art. Electrode lead 101 is designed e.g. as a shock electrode lead in this case. It has a distal section 103 and a proximal end 102 which is connected to an implanted ICD 104 (implantable cardioverter/defibrillator). This is a device that can generate shock pulses e.g. to terminate a life-threatening ventricular fibrillation. Electrode lead 101 extends through right atrium 106 and is positioned via its distal section 103 inside right ventricle 107. Distal section 103 is provided with a shock electrode 108 designed in the form of a helical wire, and which is in contact with the wall of ventricle 107. The oblong helical shape of shock electrode 108 serves to enlarge the effective electrode surface. Distal section 103 furthermore includes a ring electrode 109 and a conical point electrode 110, which can be used for purposes of palpation and/or stimulation (antibradycardia stimulation). A surface 111 of electrode lead 101 is electrically insulated except for electrodes 108-110 which are electrically conductive surface regions for transmitting electrical energy.

When a nuclear resonance tomographic examination is carried out, there is a risk—particularly to point electrode 110 which has a small surface area—that heating will occur due to the electromagnetic alternating fields that are used. This heating may cause the pacing thresholds to increase, it may impair the perceptual function, and/or result in permanent damage to the surrounding cardiac muscle tissue. As a result, electrode dislocation and/or perforation of the cardiac muscle may occur.

Figure 1:
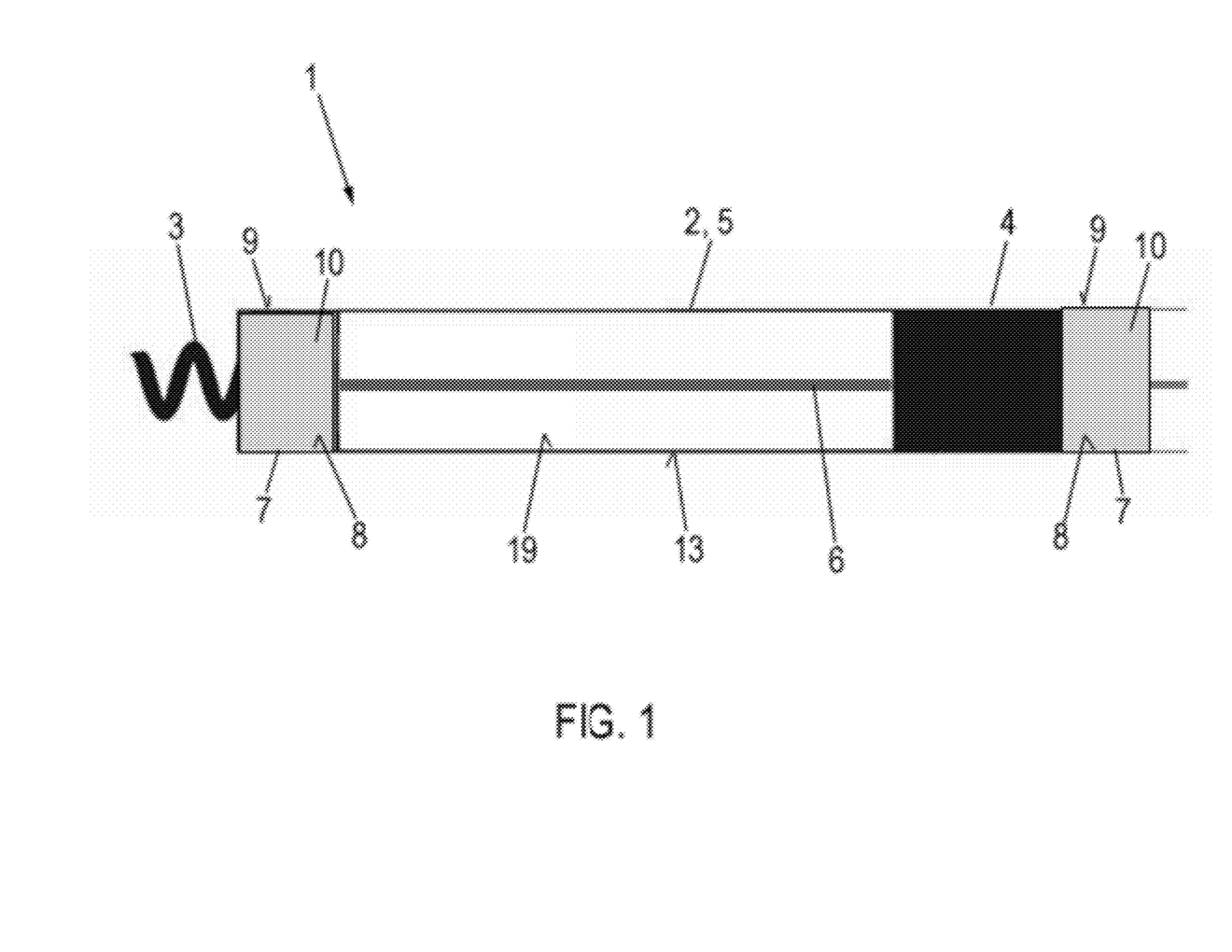
FIG. 1 a schematic depiction to illustrate an embodiment of the electrode lead according to at least one embodiment of the invention.
Figure 2:
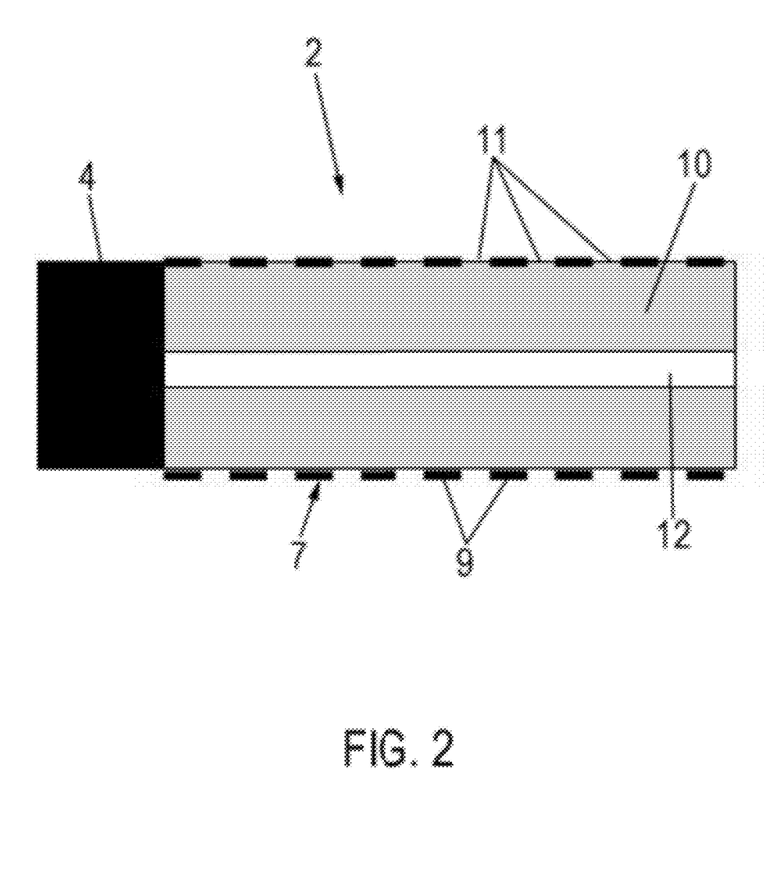
FIG. 2 an enlarged view of the distal section of the electrode lead depicted in FIG. 1.

Reference is now made to FIG. 1 and FIG. 2 which show an embodiment of electrode lead 1 according to the invention. In this case electrode lead 1 is designed as an implantable pacemaker electrode lead, as an example. It can be implanted in a patient's body in a manner analogous to that illustrated in FIG. 5, although a cardiac pacemaker (not depicted) instead of an ICD 104 will be connected to electrode lead 1.

FIG. 1, which will be considered next, shows a distal section 2 of electrode lead 1. As shown, electrode lead 1 has a tubular, flexible line body 5 that forms a line body cavity 19. Line body 5 is provided with a point electrode 3, which is designed in this case e.g. in the form of a screw-in electrode to be screwed into the cardiac tissue, and a proximally offset ring electrode 4. Point electrode 3 and ring electrode 4 are connected to an electrical lead 6 (metallic core of the conductor) disposed inside line body cavity 19; electrical lead 6 can be connected at the proximal end of electrode lead 1 to the cardiac pacemaker. Point electrode 3 can be rotated by rotating electrical lead 6 in order to permanently anchor electrode lead 1 in the cardiac muscle tissue. The anchoring of an electrode lead using a screw-in electrode is known per se to a person skilled in the art e.g. from the aforementioned publication DE 20 2006 020 517 U1, and so it need not be discussed further here.

Electrode lead 1 furthermore includes two hydrogel capsules 7, one of which is thermally coupled to point electrode 3, and the other of which is thermally coupled to ring electrode 4. Hydrogel capsules 7 are directly adjacent to electrodes 3, 4, with which they are thermally coupled, and are in physical contact with each of them. Hydrogel capsules 7 are each accommodated in line body cavity 19 in entirety. Electrical lead 6 is fed through both hydrogel capsules 7.

Each hydrogel capsule 7 includes a wall 9 composed of an elastically resilient material; wall 9 forms a capsule cavity 8 which contains a hydrogel 10. Hydrogel 10 is composed of a three-dimensional, hydrophilic polymer which, in the present embodiment, is e.g. poly(N-isopropylacrylamide) with poly-p-dioxanon as the hard segment. The swelling capacity of hydrogel 10 depends on temperature; the swelling capacity diminishes as the temperature increases. The swelling capacity of hydrogel 10 diminishes by at least 30% when temperature increases by 10° C. Walls 9 of hydrogel capsules 7 are so resilient that they can adapt to the volume of hydrogel 10 contained therein, the volume being dependent on the water content. For this purpose, walls 9 are made of a polyester having a suitable wall thickness; in the present embodiment, they can be composed of Parylene C having a large number of pinholes 11. Pinholes 11 retain hydrogel 10 but allow water to pass through, thereby enabling the water content of hydrogel 10 to change depending on its temperature. Hydrogel capsules 7 each include a passage 12 to accommodate a guide wire (not depicted) for electrode lead 1.

Point electrode and ring electrode 3, 4, respectively, are electrically conductive regions of an otherwise electrically insulated surface 13 of line body 5, via which electrical energy can be transmitted from and to the surroundings. Walls 9 of hydrogel capsules 7 each form a part of surface 13, thereby enabling water to freely enter and exit hydrogel 10. Electrodes 3, 4 are separated by a distance that is preferably in the range of 2 to 20 mm. Instead of a screw-in electrode, a point electrode 3 having a different shape could be used just as easily, e.g. a point electrode having a conical shape, as shown in FIG. 5.

During a nuclear resonance tomographic examination, the temperatures in point electrode 3 and/or ring electrode 4 can be monitored continually in electrode lead 1. To this end it is necessary to determine an outer dimension or size of the two hydrogel capsules, such as a dimension in this case that is perpendicular to the extension direction of electrode lead 1, via an evaluation of the nuclear resonance tomographic images. In this manner the temperature of point electrode and ring electrode 3, 4, respectively, can be ascertained using a simple calibration measurement, in which a correlation between the size and temperature of hydrogel capsules 7, 8 is determined.

Figure 3A:
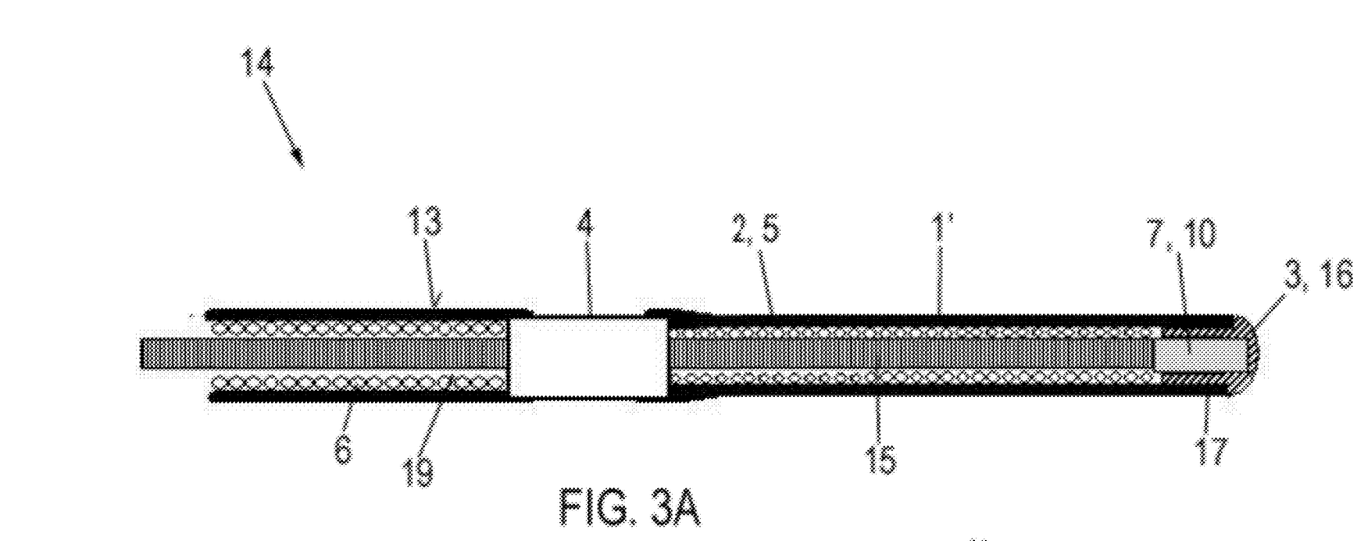
FIG. 3A-3B schematic depictions to illustrate an embodiment of the electrode lead assembly according to at least one embodiment of the invention.
Figure 3B:
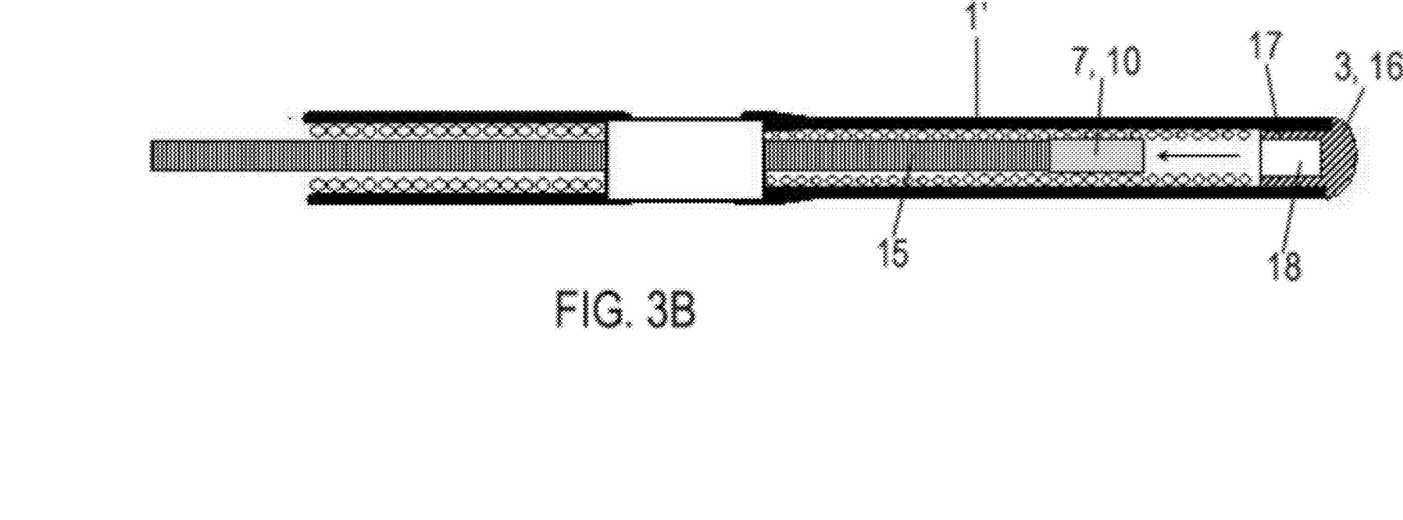

FIGS. 3A and 3B show an embodiment of electrode lead assembly according to the invention, which is labeled as a whole with reference numeral 14. Electrode lead assembly 14 includes a conventional electrode lead which does not include hydrogel capsules and is labeled as a whole with reference numeral 1'. Electrode lead assembly 14 also includes a guide wire 15 for positioning electrode lead 1'.

Electrode lead 1' includes a tubular, flexible, electrically insulated line body 5 which is provided with a point electrode 3, which is designed as a round cap, and a proximally offset ring electrode 4, each of which are electrically conductive surface regions of line body 4. Electrodes 3, 4 are electrically connected to an electrical lead 6 disposed inside line body cavity 19.

Point electrode 3 is composed of a projecting cap section 16 and a plug-in section 17 integrally formed thereon, plug-in section 17 being inserted into the distal end of line body 5 and fixedly connected thereto. Plug-in section 17 forms an electrode cavity 18 that is open on one side. Guide wire 15 includes a hydrogel capsule 7 on its distal end, hydrogel capsule 7 being fixedly connected to guide wire 15. Reference is made to the embodiments described above with regard for wall 9 and hydrogel 10 contained in hydrogel capsule 7.

When guide wire 15 is inserted into line body cavity 19 and is brought into the working position in order to position electrode lead 1', hydrogel capsule 7 enters electrode cavity 18 and is thermally coupled to point electrode 3 via physical contact (see FIG. 3A). The temperature of point electrode 3 can therefore be monitored continually via a change in an outer dimension of hydrogel capsule 7 while electrode lead 1' is being positioned. Guide wire 15 can then be removed, and hydrogel capsule 7 is drawn out of electrode cavity 18 (see FIG. 3B). In a particularly advantageous manner, a conventional electrode lead 1' can be used in this embodiment of the invention.

Figure 4:
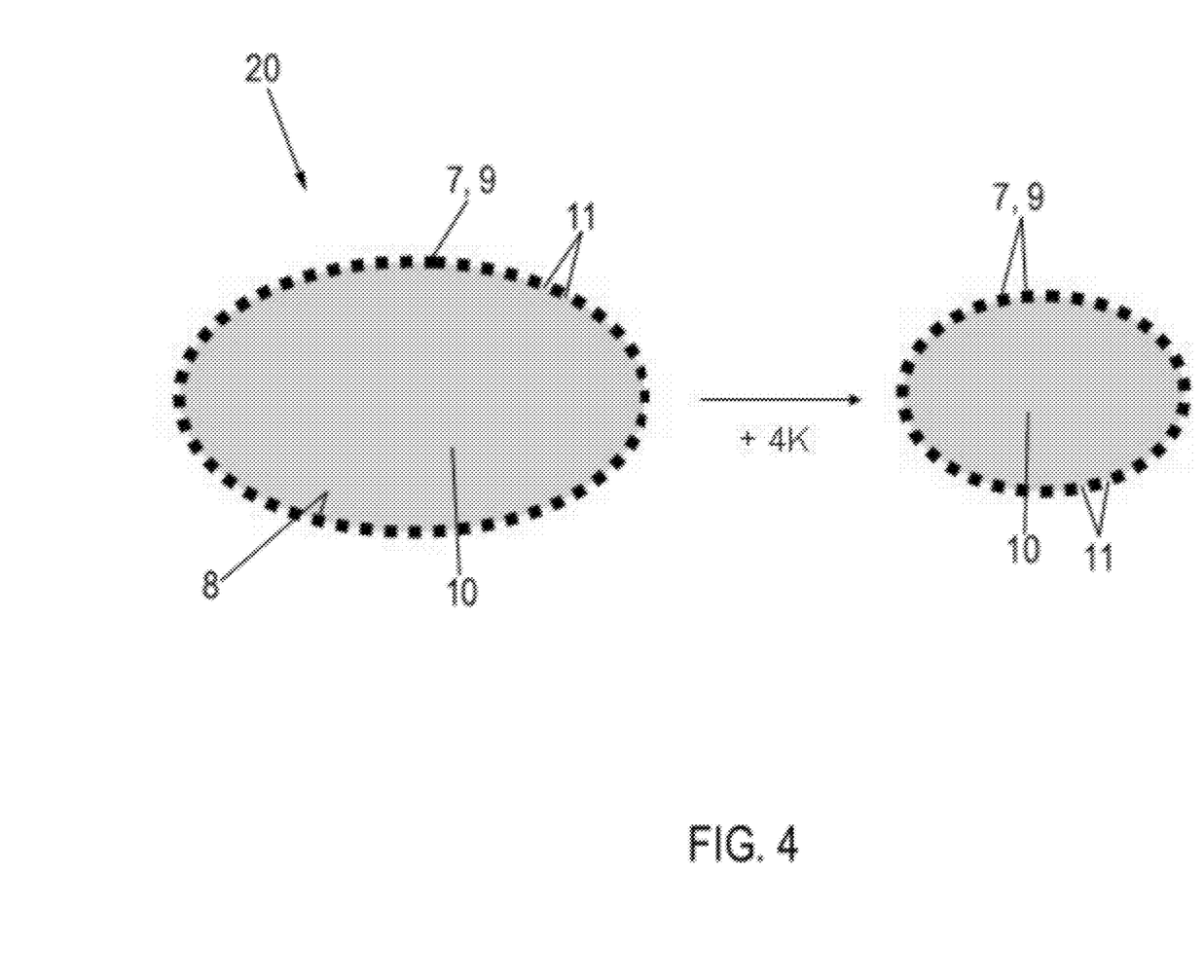
FIG. 4 a schematic depiction to illustrate an embodiment of the hydrogel sensor according to at least one embodiment of the invention.

FIG. 4 shows an embodiment of the implantable hydrogel sensor according to the invention, which is labeled as a whole with reference numeral 20. As shown, hydrogel sensor 20 includes a hydrogel capsule 7 having a resilient wall 9 which forms a capsule cavity 8 containing a hydrogel 10. Wall 9 is provided with a large number of pinholes 11 to allow water to pass from/to hydrogel 10. Reference is made to the embodiments described above with regard for wall 9 and hydrogel 10 contained in hydrogel capsule 7. Hydrogel sensor 22 can be implanted in order to detect the temperature of its surroundings via a measurement of an outer dimension or size of hydrogel capsule 7. This takes place preferably via the evaluation of a nuclear resonance tomographic image. In the embodiment shown, the temperature of implanted hydrogel sensor 20 increases by 4K, thereby resulting in a reduction in the volume of hydrogel capsule 7 due to water loss, which is clearly visible in the nuclear resonance tomographic image.

Figure 6:
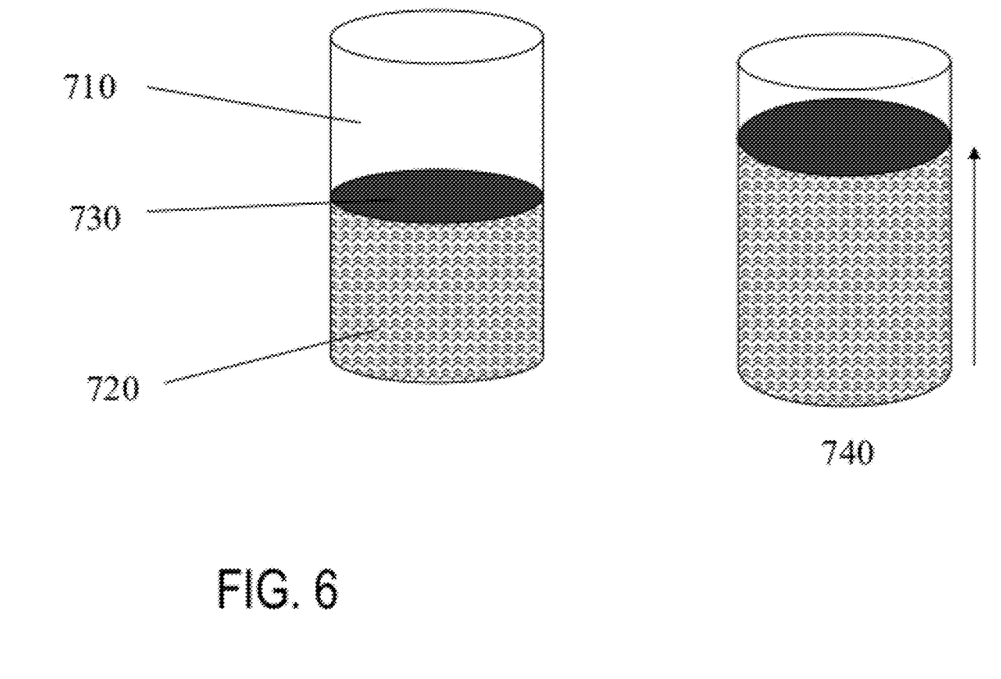
FIG. 6 a schematic depiction of a hydrogel capsule in combination with a water reservoir and a water-permeable connection/wall between the water reservoir and the hydrogel capsule.

FIG. 6 shows a hydrogel capsule in combination with a water reservoir. The electrode lead or the guide wire itself that is inserted therein contains a water reservoir 720 that is connected via a diaphragm 730 or duct to hydrogel capsule 710, and so the water-permeable wall is formed, while the rest of the hydrogel capsule is water-impermeable. Depending on the heating that occurs, the water content can therefore move between the hydrogel capsule and water reservoir 740, and the ratio of the water content can be evaluated accordingly using MRT image evaluation. This method offers the advantage that it can also be used in a component, such as the guide wire, that is insulated against the bodily fluid, and that no calibration or only very simple calibration is required to evaluate the ratio of the water content.

As explained extensively with reference to the embodiments, at least one embodiment of the invention makes it possible, via the thermal coupling of electrodes to hydrogel capsules, to easily and reliably determine the temperature of the electrodes during a nuclear resonance tomographic examination, thereby making it possible to take nuclear resonance tomographic images even of patients who have an implanted electrode probe. Electrode leads and electrode lead assemblies according to the invention are characterized by a particularly simple use in practice and can be manufactured easily and cost effectively in high-volume production.

In addition, at least one embodiment of the invention makes it possible to automatically control a nuclear resonance tomograph, wherein the intensity, for instance, of the electromagnetic alternating fields used for resonance excitation is reduced on the basis of the temperature of one or more electrodes of an implanted electrode lead, if the temperature of the electrode exceeds a predeterminable first threshold value. As an alternative, the electromagnetic alternating fields can be shut off entirely if the temperature of an electrode exceeds a predeterminable second temperature threshold value. The first and the second temperature threshold value can be the same or different. Likewise, the temperature of one or more electrodes can be displayed in a graphical display device. An optical and/or acoustic warning signal can also be output as soon as the temperature of an electrode reaches a temperature threshold value of this type. It would also be feasible to specifically apply an electrical pulse to an electrode in order to ablate surrounding bodily tissue. The temperature of the electrode can be easily monitored and controlled via the thermally coupled hydrogel capsule.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable electrode lead comprising:
a distal section having at least one electrode configured to transmit electrical energy between the implantable electrode lead and an area that surrounds said implantable electrode lead;
wherein the implantable electrode lead includes at least one hydrogel capsule that is thermally coupled to the at least one electrode;
said at least one hydrogel capsule comprising
at least one water-permeable wall that forms a cavity containing a volume of a hydrogel having a temperature-dependent swelling capacity;
wherein at least parts of the at least one water-permeable wall of the at least one hydrogel capsule are configured to adapt to the volume of the hydrogel.

2. The electrode lead according to claim 1, wherein the at least one hydrogel capsule abuts the at least one electrode and has physical contact therewith.

3. The electrode lead according to claim 1, wherein the at least one electrode comprises a point electrode disposed on the distal section of the implantable electrode lead.

4. The electrode lead according to claim 1, wherein the at least one hydrogel capsule is situated in the implantable electrode lead, and wherein the at least one water-permeable wall of the hydrogel capsule forms a region of a surface of the implantable electrode lead.

5. The electrode lead according to claim 4, wherein the at least one hydrogel capsule and the hydrogel contained are configured to provide a passage for a guide for the implantable electrode lead.

6. The electrode lead according to claim 1, wherein the temperature-dependent swelling capacity of the hydrogel diminishes as temperature increases.

7. The electrode lead according to claim 1, wherein said at least one hydrogel capsule further comprises an outer dimension configured to be measured; and,
wherein said at least one electrode further comprises a temperature configured to be determined based on the outer dimension of the at least one hydrogel capsule.

8. The electrode lead according to claim 7, wherein the outer dimension of the at least one hydrogel capsule is configured to be measured with a nuclear resonance tomographic image.

9. The electrode lead according to claim 1, wherein the at least one water-permeable wall comprises a plurality of pinholes in order to allow water to pass to and from the hydrogel.

10. An electrode lead assembly for a medical application, comprising:
an implantable electrode lead comprising
a distal section with at least one electrode configured to transmit electrical energy between the implantable electrode lead and an area that surrounds said implantable electrode lead;
a guide, configured to be inserted into the implantable electrode lead, and configured to guide the electrode implantable lead wherein the guide comprises
at least one hydrogel capsule comprising
a wall that is water-permeable at least in sections and forms a cavity containing a volume of a hydrogel having a temperature-dependent swelling capacity;
the wall of the at least one hydrogel capsule configured to adapt to the volume of the hydrogel;
wherein the at least one hydrogel capsule is configured to thermally couple to the at least one electrode in a position of the guide that is configured to guide the implantable electrode lead.

11. The electrode lead assembly according to claim 10, further comprising a water reservoir and a diaphragm or duct wherein the water reservoir is connected via the diaphragm or the duct to the at least one hydrogel capsule, via the wall that is water-permeable, while the rest of the at least one hydrogel capsule is either water-permeable or water-impermeable.

12. The electrode lead assembly according to claim 10, further comprising a water reservoir and wherein the wall that is water-permeable comprises a diaphragm or duct or opening, wherein the at least one hydrogel capsule is connected to the water reservoir via the wall that is water-permeable and the walls that do not abut the water reservoir are either water-permeable or water-impermeable.

13. The electrode lead according to claim 10, wherein said at least one hydrogel capsule further comprises an outer dimension configured to be measured; and,
wherein said at least one electrode further comprises a temperature configured to be determined based on the outer dimension of the at least one hydrogel capsule.

14. The electrode lead according to claim 13, wherein the outer dimension of the at least one hydrogel capsule is configured to be measured with a nuclear resonance tomographic image.

15. The electrode lead according to claim 10, wherein the at least one water-permeable wall comprises a plurality of pinholes in order to allow water to pass to and from the hydrogel.

16. An implantable hydrogel sensor comprising:
    a hydrogel capsule having a wall that is water-permeable at least in sections and forms a cavity,
    a volume of a hydrogel having a temperature-dependent swelling capacity contained in the cavity;
    wherein the wall is configured to adapt to the volume of the hydrogel;
    wherein said implantable hydrogel sensor is configured to couple with an implantable electrode lead or a guide for an implantable electrode lead; and
    wherein said implantable hydrogel sensor is configured to allow an ambient temperature of the implantable hydrogel sensor to be determined.

* * * * *